(12) United States Patent
Hays et al.

(10) Patent No.: US 9,808,254 B2
(45) Date of Patent: Nov. 7, 2017

(54) SELECTIVE AORTIC BALLOON OCCLUSION DEVICE, METHODS OF USE, AND USES THEREOF

(71) Applicant: HAYS INC., Onsted, MI (US)

(72) Inventors: Gregory Hays, Onsted, MI (US); Julia Hays, Onsted, MI (US)

(73) Assignee: Hays, Inc., Onsted, MI (US)

( * ) Notice: Subject to any disclaimer, the term of this patent is extended or adjusted under 35 U.S.C. 154(b) by 149 days.

(21) Appl. No.: 14/830,445

(22) Filed: Aug. 19, 2015

(65) Prior Publication Data

US 2017/0049457 A1    Feb. 23, 2017

(51) Int. Cl.
*A61B 17/12* (2006.01)
*A61M 29/02* (2006.01)

(52) U.S. Cl.
CPC .. *A61B 17/12122* (2013.01); *A61B 17/12022* (2013.01); *A61M 29/02* (2013.01)

(58) Field of Classification Search
CPC ........ A61B 17/12122; A61B 17/12136; A61B 2017/12127; A61B 17/00234; A61B 17/12022; A61B 17/12027; A61B 17/12031; A61B 17/12036; A61B 17/1204; A61B 17/12045; A61B 17/12109; A61B 2017/00243; A61B 2017/12054; A61M 2025/1015; A61M 2025/1095; A61M 2025/1097; A61M 2025/1052; A61M 39/22; A61M 25/0029; A61M 25/003; A61M 35/0075; A61M 2025/0004

See application file for complete search history.

(56) References Cited

U.S. PATENT DOCUMENTS

| | | | |
|---|---|---|---|
| 5,320,605 A | 6/1994 | Sahota | |
| 5,370,617 A | 12/1994 | Sahota | |
| 5,505,701 A | 4/1996 | Anaya Fernandez de Lomana | |
| 6,027,519 A | 2/2000 | Stanford | |
| 8,603,064 B2 | 12/2013 | Hattangadi et al. | |
| 8,728,053 B2 | 5/2014 | Broaddus et al. | |
| 2004/0220521 A1 | 11/2004 | Barbut | |

(Continued)

FOREIGN PATENT DOCUMENTS

| | | |
|---|---|---|
| EP | 2560722 A2 | 2/2013 |
| WO | 2011133736 A2 | 10/2011 |

OTHER PUBLICATIONS

Notification of Transmittal, International Search Report and the Written Opinion of the ISA, dated Nov. 11, 2016, from corresponding International Application PCT/US2016/047410, 13 pages.

*Primary Examiner* — Eric Rosen
*Assistant Examiner* — Brooke Labranche
(74) *Attorney, Agent, or Firm* — Young Basile Hanlon & MacFarlane, P.C.

(57) ABSTRACT

A selective aortic balloon device includes a catheter comprising an open distal end configured to be inserted into a body cavity or vessel, and a plurality of adjustable port regions with inflatable balloons between adjacent adjustable port regions. Each adjustable port region is configured to move between a closed position and an open position to selectively allow fluid flow to enter the catheter through the open distal end and to exit the catheter through one or more of the plurality of adjustable port regions depending on an inflation pattern of the inflatable balloons.

19 Claims, 9 Drawing Sheets

(56) References Cited

U.S. PATENT DOCUMENTS

| | | |
|---|---|---|
| 2011/0034948 A1 | 2/2011 | Ravikumar |
| 2013/0327113 A1 | 12/2013 | Green |
| 2015/0352338 A1* | 12/2015 | Kassab .............. A61B 5/02152 604/67 |

* cited by examiner

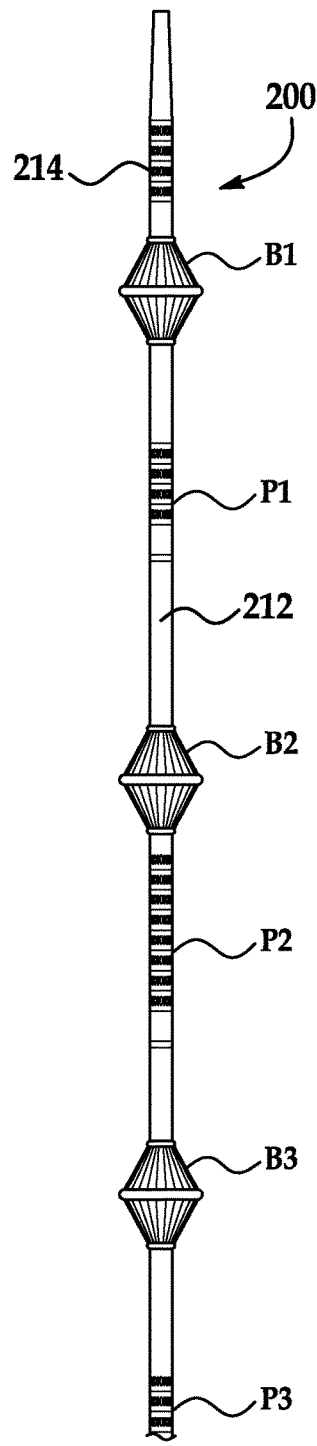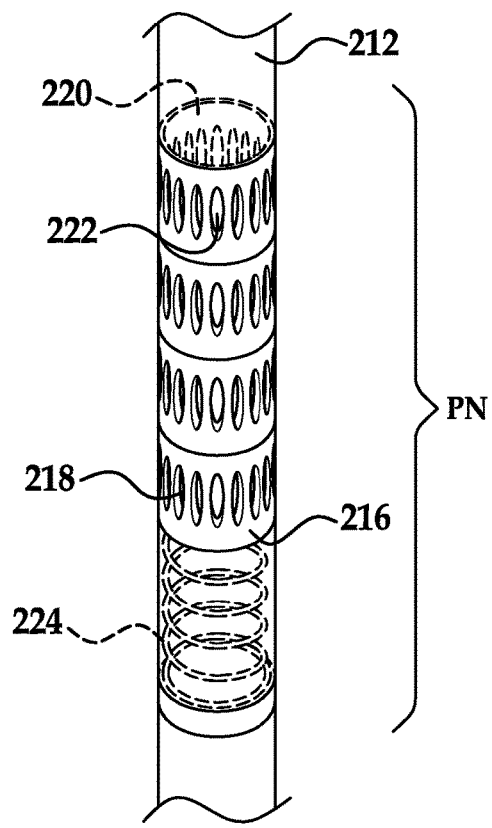
FIG. 10
FIG. 11

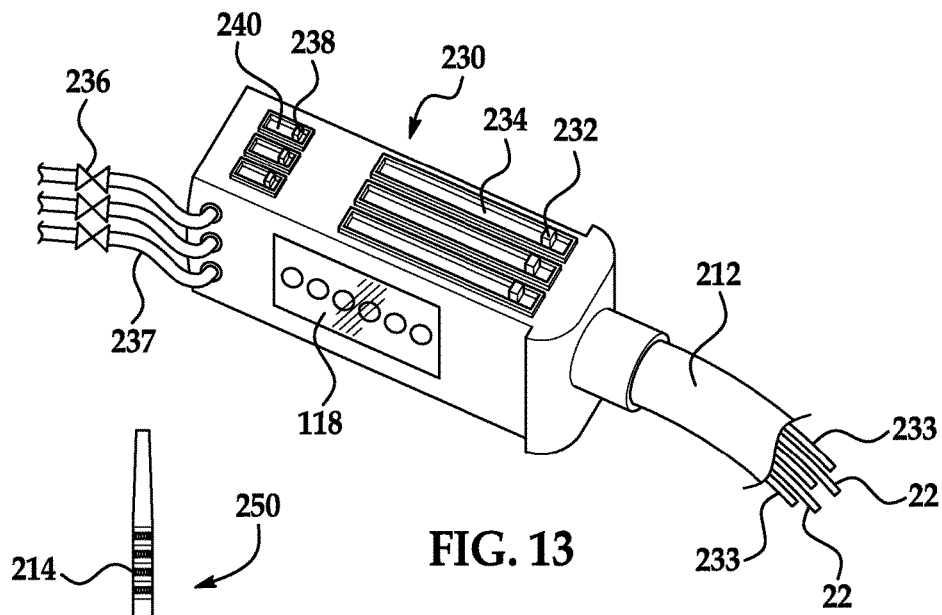
FIG. 13
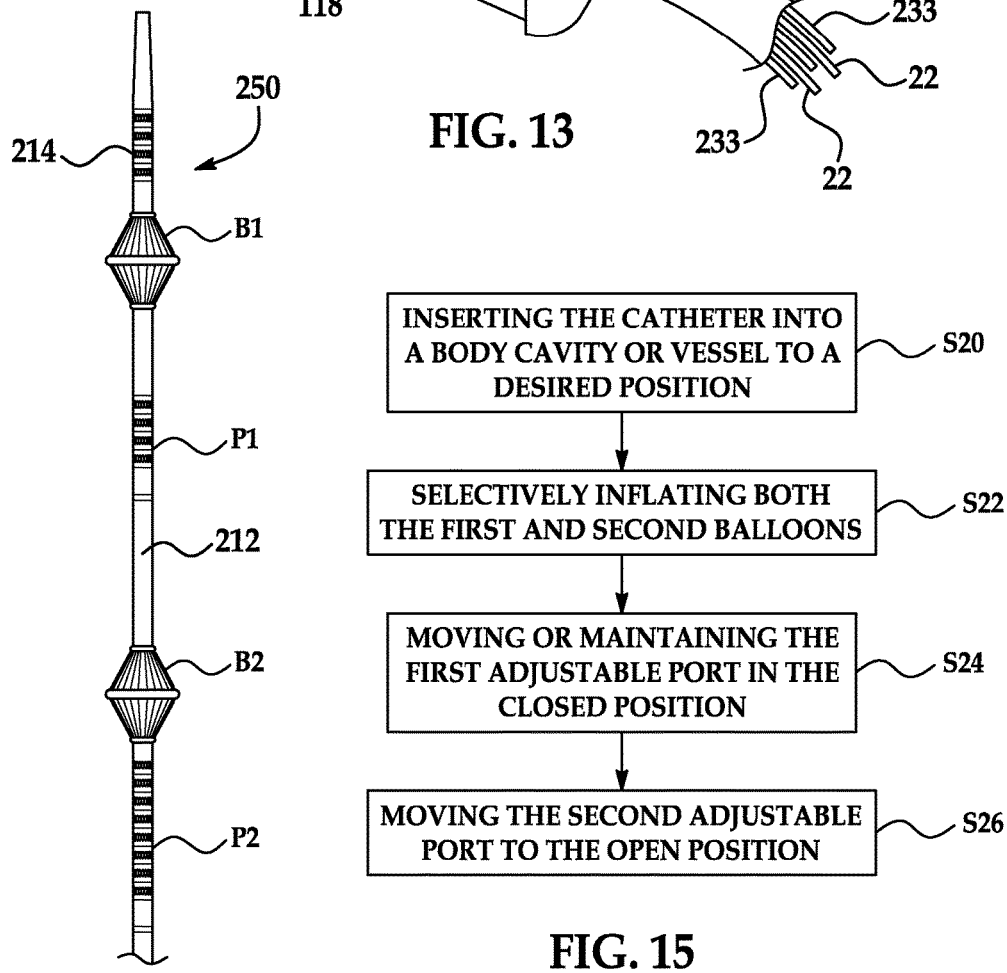
FIG. 14
FIG. 15

SELECTIVE AORTIC BALLOON OCCLUSION DEVICE, METHODS OF USE, AND USES THEREOF

CROSS-REFERENCE TO RELATED APPLICATION

This application is related to co-pending application Ser. No. 14/830,342 entitled "NARROW PROFILE BALLOON FOR USE WITH AN OCCLUSION DEVICE, METHODS OF USE, AND USES THEREOF" which is incorporated herein by reference in its entirety.

TECHNICAL FIELD

The disclosure herein relates in general to aortic balloon occlusion devices, and in particular, to selective, resuscitative aortic balloon occlusion devices, methods of use, and uses thereof.

BACKGROUND

Conventional afterload enhancement devices include, as examples, the MAST, introduced in 1903, the aortic cross clamp, and the resuscitative endovascular balloon occlusion of the aorta. Each of these devices has drawbacks that limit their effectiveness and uses. As non-limiting examples, the current technology offers an all-or-nothing approach to intra-abdominal bleeding, poor control over reperfusion, no ability to maintain renal and distal perfusion with intra-abdominal bleeding, difficult precise placement of the balloon or balloons, and a crude estimation of pressure applied to vasculature that can result in aortic rupture.

SUMMARY

Disclosed herein is a narrow profile balloon for use with a catheter that allows for precise placement of the balloon and accurate estimation of the pressure applied to the vasculature, along with other advantages described herein.

One embodiment of a narrow profile balloon for use with a catheter as disclosed herein comprises an anchored end fixed to the catheter, a movable end distal to the fixed end, a wall extending between the anchored end and the movable end, an inflatable tube located along the wall and circumscribing the wall, and at least one tension wire attached to the movable end and extending through the catheter such that the at least one tension wire is accessible to move the movable end of the balloon towards the anchored end when the catheter is positioned in a body cavity.

Disclosed herein are embodiments of an aortic occlusion device. One embodiment of an aortic occlusion device comprises a catheter and a balloon mounted along the catheter, wherein the balloon is a narrow profile balloon. The narrow profile balloon comprises an anchored end fixed to the catheter, a movable end distal to the fixed end, a wall extending between the anchored end and the movable end, an inflatable tube located proximate along the wall and circumscribing the wall, and at least one tension wire attached to the movable end and extending through the catheter such that the at least one tension wire is accessible to move the movable end of the balloon towards the anchored end when the catheter is positioned in the aorta.

Also disclosed herein are methods of using the narrow profile balloon and the aortic occlusion device. One such method of using the aortic occlusion device, where the aortic occlusion device has a plurality of balloons, at least one of the plurality of balloons being the narrow profile balloon, comprises inserting the catheter into a body cavity or vessel within a human or animal body, positioning the catheter such that a distal balloon of the plurality of balloons is located proximate a diaphragm, selectively inflating the inflatable tube of the narrow profile balloon, and placing tension on the at least one tension wire attached to the movable end of the narrow profile balloon to move the movable end towards the anchored end, thereby moving the inflated tube to contact a wall of the aorta, blocking blood flow below the inflated tube.

Uses of the narrow profile balloon and the aortic occlusion device are also disclosed herein.

Also disclosed herein are selective aortic balloon occlusion devices. One embodiment of a selective aortic balloon device comprises a catheter comprising an open distal end and a plurality of adjustable port regions with inflatable balloons between adjacent adjustable port regions. Each adjustable port region is configured to move between a closed position and an open position to selectively allow fluid flow to enter the catheter through the open distal end and to exit the catheter through one or more of the plurality of adjustable port regions depending on a pattern of one or more inflated balloons.

Another embodiment of a selective aortic balloon device comprises a catheter comprising a distal end configured to be inserted into a body cavity or vessel, the distal end having at least one opening, a first balloon downstream of the open distal end, a first adjustable port region downstream of the first balloon, and a second balloon downstream of the first adjustable port region and upstream of a closed proximate end. The first adjustable port region is configured to move between an open position and a closed position, wherein the open position allows flow into the distal end through the catheter and exiting through the first adjustable port region and the closed position prevents flow through the first adjustable port region.

In the embodiments of selective aortic balloon devices, the first adjustable port region can comprise an outer catheter tube having at least one outer aperture through an outer catheter tube wall, an inner tube sized to movably fit within the outer catheter tube and having at least one inner aperture through an inner tube wall, and a biasing member attached to the inner tube, biasing the inner tube so that the at least one inner aperture and the at least one outer aperture are offset in the closed position. The biasing member is configured to move the inner tube to gradually overlap the at least one inner aperture and the at least one outer aperture through intermediate positions to the open position, where the at least one inner aperture and the at least one outer aperture are fully aligned.

In the embodiments of selective aortic balloon devices, the device can further comprise a second adjustable port region downstream of the second balloon and a third balloon downstream of the second adjustable port region, wherein the second adjustable port region is configured to move between an open position and a closed position.

In the embodiments of selective aortic balloon devices, the device can further comprise a third adjustable port region downstream of the third balloon and upstream of a closed proximate end, wherein the third adjustable port region is configured to move between an open position and a closed position.

Also disclosed are methods of using the selective aortic balloon devices disclosed herein. One method includes selectively inflating at least the first balloon and maintaining or moving with the external controller the first adjustable port region to the closed position to stop blood flow downstream of the inflated first balloon. The method can also include inflating the second balloon and maintaining or moving with the external controller the first adjustable port region to the open position, thereby stopping blood flow downstream of the inflated second balloon while allowing blood to flow through the first adjustable port region.

Another method of using the selective aortic balloon occlusion devices includes inflating the third balloon, maintaining or moving the first adjustable port region to the open position, and maintaining or moving the second adjustable port region to the open position, thereby stopping blood flow downstream of the inflated third balloon while allowing blood to flow through the catheter through the distal end and out through the first adjustable port region and the second adjustable port region.

Another method of using the selective aortic balloon occlusion devices includes inflating one or both of the first balloon and the second balloon, maintaining or moving the first adjustable port region to the closed position, and maintaining or moving the second adjustable port region to the open position, thereby stopping blood flow downstream of the inflated second balloon while allowing blood to flow through the catheter into the distal end and out through the second adjustable port region.

Another method of using the selective aortic balloon occlusion devices includes inflating the second balloon and the third balloon, maintaining or moving the first and third adjustable port regions to the open position, and maintaining or moving the second adjustable port region to the closed position, thereby preventing blood flow through the second adjustable port region while allowing blood flow through the first adjustable port region and the third adjustable port region.

Another method of using the selective aortic balloon occlusion devices includes inflating the third balloon, maintaining or moving the first adjustable port region and the second adjustable region to the closed position, and maintaining or moving the third adjustable port region to the closed position, thereby bypassing blood flow through the catheter to exit through the third adjustable port region.

Another method of using the selective aortic balloon occlusion devices includes inflating the third balloon, maintaining or moving the first adjustable port region to the open position, maintaining or moving the third adjustable port region to the closed position, and maintaining or moving the second adjustable port region to the open position, thereby providing blood flow through the catheter to exit through the first and second adjustable port regions while preventing blood flow through the third adjustable port region.

Variations in these and other aspects, features, elements, implementations, and embodiments of the methods, apparatus, procedures, and algorithms disclosed herein are described in further detail hereafter.

BRIEF DESCRIPTION OF THE DRAWINGS

The various aspects of the methods and apparatuses disclosed herein will become more apparent by referring to the examples provided in the following description and drawings in which:

FIG. 10 is a side view of an embodiment of a selective aortic balloon occlusion device;

FIG. 11 is an enlarged view of an adjustable port region of the selective aortic balloon occlusion device of FIG. 10;

FIG. 13 is a perspective view of an external controller for the narrow profile balloons and the adjustable port regions;

FIG. 14 is a side view of another embodiment of a selective aortic balloon occlusion device;

FIG. 15 is a flow diagram of a method of using the selective aortic balloon occlusion device of FIG. 14;

DETAILED DESCRIPTION OF THE EMBODIMENTS

Disclosed herein is a narrow profile balloon illustrated in FIGS. 1-4 for use on a catheter which is placed in a body cavity of a human or an animal. This device enables the deployment of the narrow profile balloon for use within cavities with limited space, such as blood vessels. The narrow profile balloon allows for precise placement between vessels unlike any conventional balloons. For example, the narrow profile balloon can be precisely placed in the aorta between the renal trunk and the celiac trunk, without blocking either trunk directly. Conventional balloons have longitudinally extended walls that are expanded and contact a longitudinally extended area of the cavity such as a vessel. This longitudinal wall of the balloon makes it difficult to precisely position the balloon between closely spaced trunks without blocking one or both of the trunks.

The narrow profile balloon as used herein refers to a flexible tube as well as the mounting frame structure of the flexible tube. The flexible tube can be inflatable with fluid such as air, or can be a soft seal of a material such as rubber, mounted on a contractible and expandable frame. The frame is permanently attached at its proximal end and is mobile at its distal end. The distal end is attached to tension cords, which allow the user to expand the device in order to safely occlude a vessel, as a non-limiting example.

Figure 1:
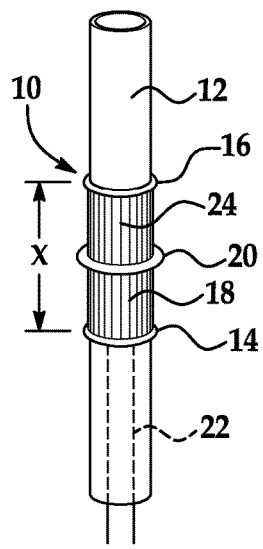
FIG. 1 is a perspective view of a narrow profile balloon on a catheter.
Figure 2:
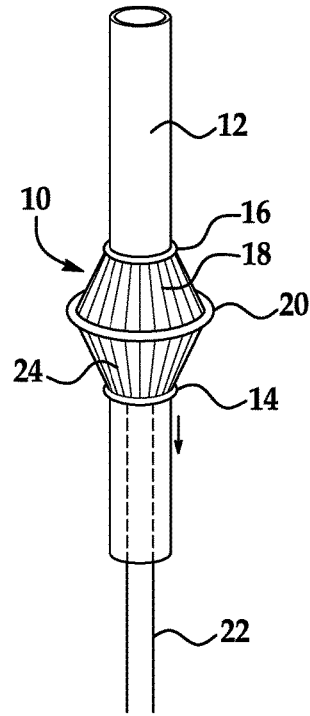
FIG. 2 is a perspective view of the narrow profile balloon of FIG. 1 in a partially contracted state on a catheter.
Figure 3:
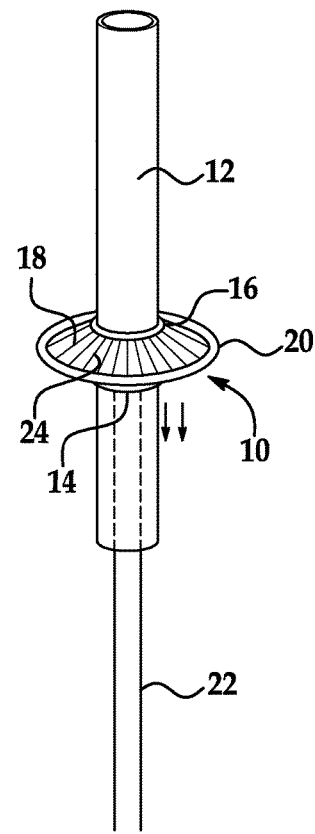
FIG. 3 is a perspective view of the narrow profile balloon of FIG. 1 in a fully contracted state on a catheter.
Figure 4:
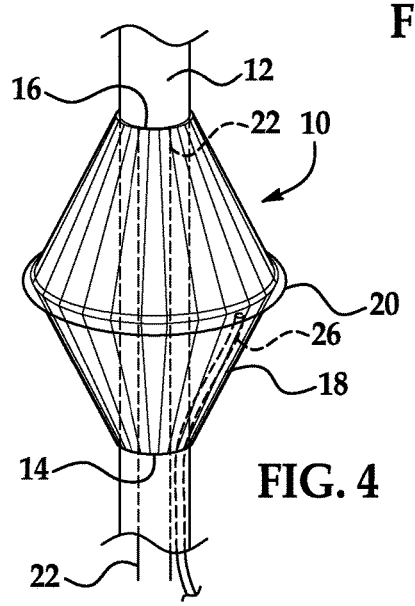
FIG. 4 is a perspective view of the narrow profile balloon of FIG. 2 with the catheter and tension wires shown in broken line.

As shown in FIGS. 1-3, a narrow profile balloon 10 for use with a catheter 12 comprises an anchored end 14 fixed to the catheter 12, a movable end 16 distal to the fixed end 14, a wall 18 extending between the anchored end 14 and the movable end 16, a flexible tube 20 located along the wall 18 and circumscribing the wall 18, and at least one tension wire 22 attached to the movable end 16 and extending through the catheter 12 such that an end of the at least one tension wire 22 is accessible outside of the catheter 12. When the at least one tension wire 22 is tensioned by a user, the movable end 16 of the balloon 10 moves toward the anchored end 14, thereby moving the flexible tube 20 toward a wall of a body cavity in which the catheter 12 is positioned.

The flexible tube 20 is mounted on a frame that includes the wall 18, the movable end 16 and the anchored end 14. The wall 18 can be made of a material such as rubber or a flexible plastic. The frame can include support 24 such as semi-stiff wires which can be embedded in the material of the wall 18 or can be internal to the material of the wall 18 to maintain the shape of the wall 18 as the balloon 10 is tensioned. The support 24 can be a metal, plastic, resin, ceramic or fiber materials, as non-limiting examples, that have sufficient rigidity to maintain the shape of the wall 18. The support 24 can extend the length of the wall 18 with a portion aligned with the flexible tube 20 that bends, or the support 24 can extend along the wall 18 from the flexible tube 20 to each of the movable end 16 and the anchored end 14. The anchored end 14 and the movable end 16 can be non-flexible rings of material embedded in opposing ends of the wall 18. The flexible tube 20 can be positioned as shown, along a longitudinal center X of the wall 18 as a non-limiting example. The flexible tube 20 circumscribes the exterior of the wall 18 so that when the narrow profile balloon 10 is tensioned, the flexible tube 20 is the only portion of the narrow profile balloon 10 that contacts a wall of the cavity in which the catheter 12 is inserted. As used herein, "cavity" can mean organ, artery, vein, or other internal body cavity in which the narrow profile balloon can be used for any purpose.

When the catheter 12 is inserted into a body cavity, the narrow profile balloon 10 is extended to its full length, as shown in FIG. 1, with no or insufficient tension on the tension wire 22 to move the movable end 16 toward the anchored end 14. Once the catheter 12 is placed in the body cavity, the at least one tension wire 22 is pulled with the end external to the catheter 12 and body to move the movable end 16 toward the anchored end 14, as shown in FIG. 2. The wall 18 is configured to fold at the flexible tube 20 when tension is placed on the tension wire 22. As shown in FIG. 3, the tension wire 22 is pulled to its desired tension, with the flexible tube 20 resting against a wall of the cavity.

The flexible tube 20 can be inflatable with a fluid such as air. The inflatable tube 20 can have an inflation valve 26 (illustrated in FIG. 4) accessible for inflation when the catheter 12 is positioned in the body cavity. The inflatable tube 20 can be inflated via a small tube which is embedded within the wall 18 of the narrow profile balloon 10 and through the catheter 20 to an inflation device exterior the catheter 12 and the body. Alternatively, the inflatable tube 20 can be inflated prior to insertion of the catheter 12 with the wall 18 fully extended as shown in FIG. 1.

Figure 5:
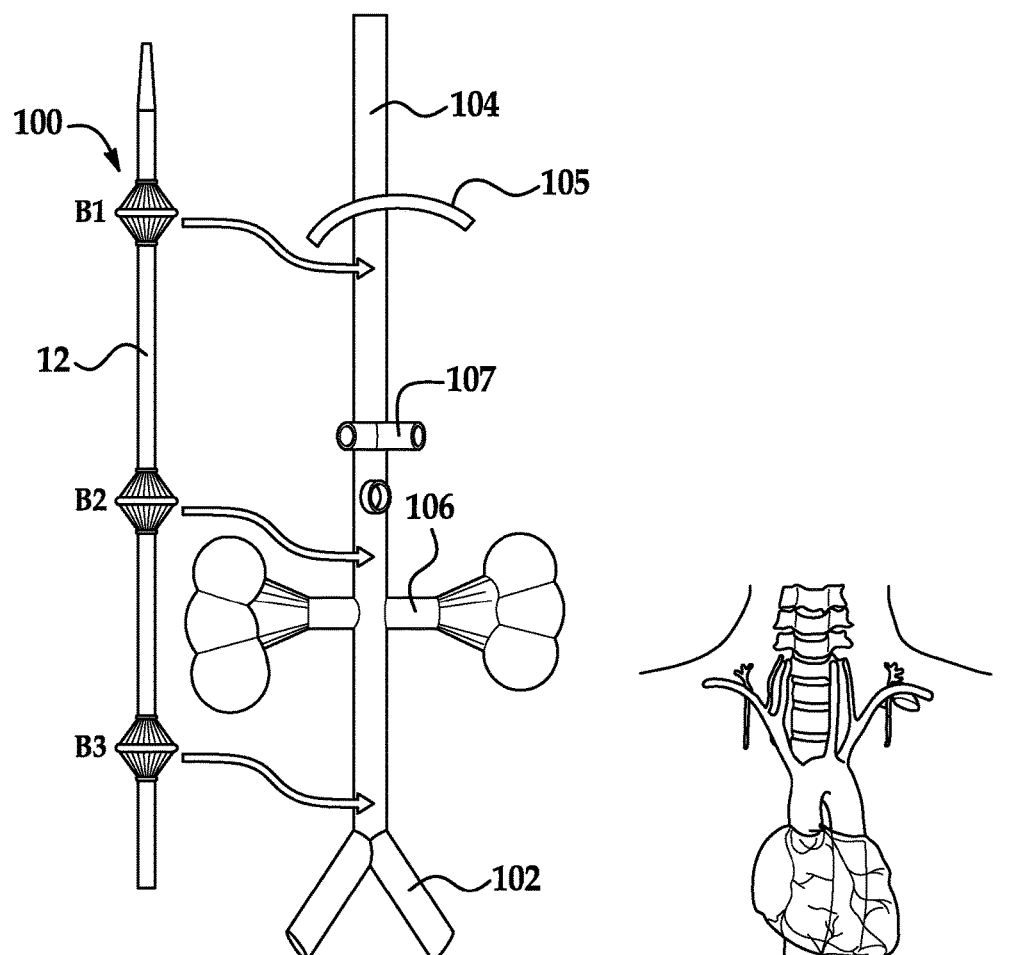
FIG. 5 is a side view of a catheter having three narrow profile balloons illustrating placement of the narrow profile balloons along a descending aorta.

FIG. 5 illustrates an example of an aortic occlusion device 100. Although the aortic occlusion device illustrates the use of three narrow profile balloons 10, one or more narrow profile balloons 10 can be used with a catheter 12. Alternatively, one or more narrow profile balloons 10 can be used in combination with conventional balloons. For example, a catheter 12 can include a plurality of balloons, with an intermediate balloon being the narrow profile balloon 10 configured on the catheter 12 to allow for placement of the flexible tube 20 between two arterial ports. Alternatively, the catheter 12 can include all narrow profile balloons 10.

Figure 6:
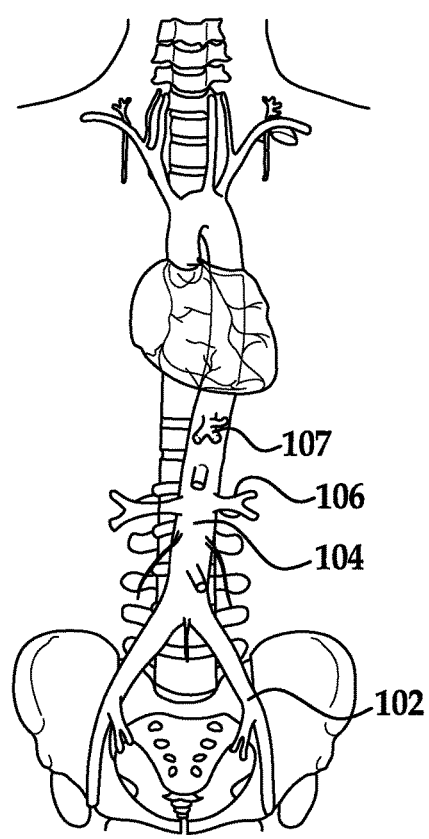
FIG. 6 is an illustration of the descending aorta in a human body.

The aortic occlusion device 100 shown in FIG. 5 has three narrow profile balloons B1, B2, B3. One example of use of such an aortic occlusion device 100 is for insertion into a femoral artery 102 of a body into the descending aorta 104. FIG. 6 depicts the femoral artery 102 in relation to the heart and pelvic area for illustrative purposes only. In the aortic occlusion device illustrated in FIG. 5, the distal narrow profile balloon B1 is spaced from the intermediate narrow profile balloon B2 such that the distal narrow profile balloon B1 is located proximate a diaphragm 105 in an adult body. A third narrow profile balloon B3 is spaced from the intermediate narrow profile balloon B2 opposite the distal narrow profile balloon B1 such that the intermediate narrow profile balloon B2 and the third narrow profile balloon B3 span renal ports 106 in the adult body.

Figure 7A:
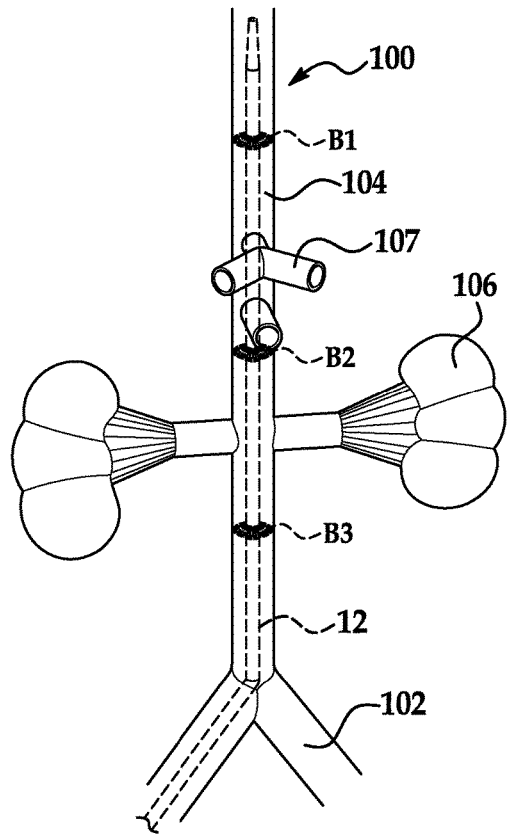
FIG. 7A is an illustration of the catheter of FIG. 5 in the descending aorta with all three of the narrow profile balloons in a fully contracted position.
Figure 7B:
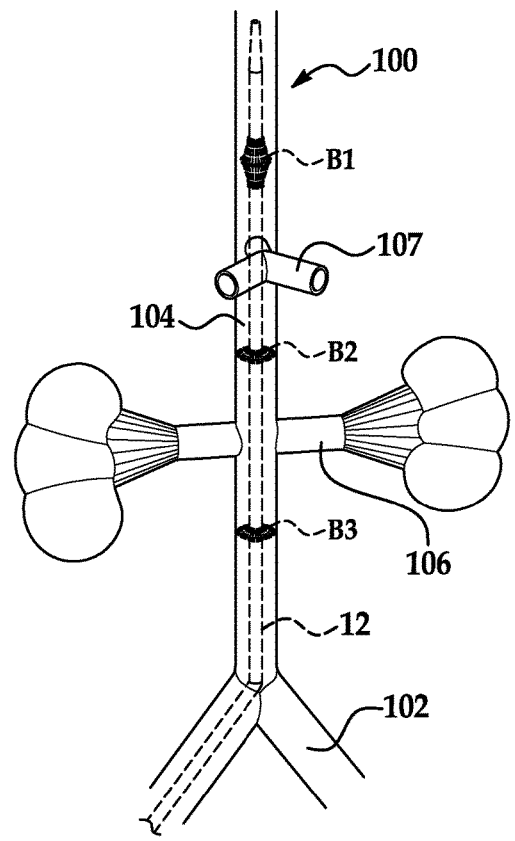
FIG. 7B is an illustration of the catheter of FIG. 5 in the descending aorta with one of the narrow profile balloons extending along the catheter and two of the narrow profile balloons in a fully contracted position.

Each of narrow profile balloons B1, B2, B3 is selectively inflated, if the flexible tube is inflatable, and tensioned with the respective tension wire(s) 22, when the catheter 12 is positioned within the cavity of the body. As a non-limiting example, when the catheter 12 is a closed catheter and is positioned in the aorta 104 through the femoral artery 102, the distal narrow profile balloon B1 can be tensioned to stop blood flow below the diaphragm. All three narrow profile balloons B1, B2, B3 can be tensioned as illustrated in FIG. 7A, so that when blood is ready to be introduced below the diaphragm, tension on the narrow profile balloons B1, B2, B3 can be slowly and sequentially released to slowly introduce blood flow and avoid a sudden drop in blood pressure, which is typical with conventional devices. As illustrated in FIG. 7B, the intermediate narrow profile balloon B2 and the third narrow profile balloon B3 can be tensioned, with the distal narrow profile balloon B1 in its released state, to allow blood flow to celiac ports 107 but prevent blood flow in the descending aorta 104 beyond the celiac ports 107. The third narrow profile balloon B3 can be tensioned, with the intermediate and distal narrow profile balloons B1, B2 in their released state, to allow blood to flow to the renal ports 106 but prevent blood to flow in the descending aorta 104 beyond the renal ports 106.

Figure 8:
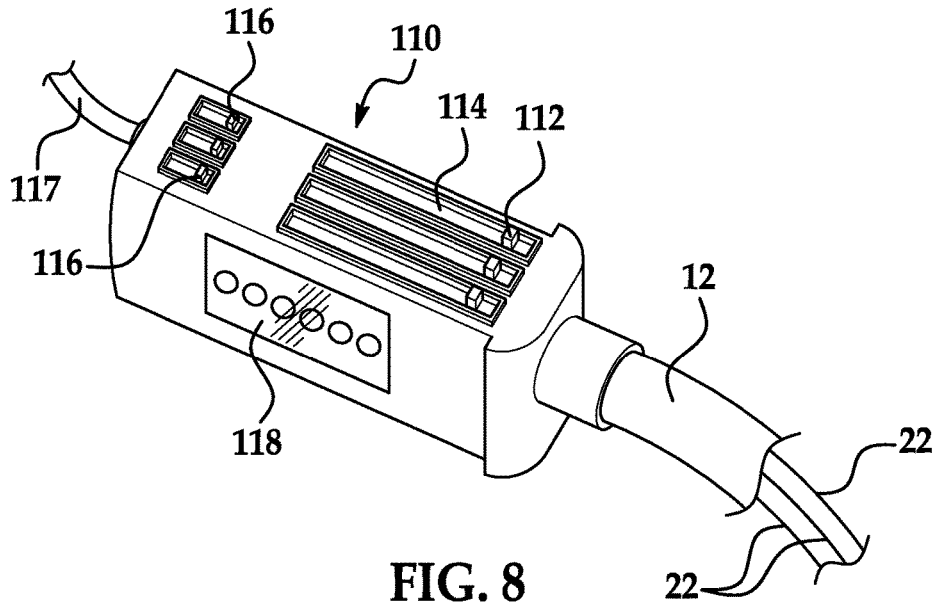
FIG. 8 is a perspective view of an external controller for the narrow profile balloons.

The aortic occlusion device 100 can further comprise an external control 110, illustrated in FIG. 8, engaged with the at least one tension wire 22 of each of the narrow profile balloons (for example, B1, B2, B3) included in the device 100 and configured to selectively pull or release each of the at least one tension wire 22 to move the flexible tube 20 of each narrow profile balloon toward a wall of the aorta 104. As a non-limiting example, the external control 110 can have sliders 112, each slider 112 connected to a tension wire(s) 22 of a narrow profile balloon. The sliders 112 can be individually moved to any position along a respective track 114 to thereby move the narrow profile balloon to or from a closed, partially open or open position. The sliders 112 are configured to lock in place after positioned to the desired point along the respective track 114, such as by pushing the slider 112 in or pulling the slider 112 outward to a locking position. The external control 110 can also be engaged with the inflation valve 26 associated with a respective narrow profile balloon and configured to selectively expand the inflatable tube 20 of the narrow profile balloon. As a non-limiting example, the external control 110 can include a switch 116 that activates a valve that is connected to a fluid supply, such as air, through a fluid supply conduit 117. Each narrow profile balloon of an aortic occlusion device will be associated with a switch 116 to selectively inflate and deflate as required.

The sliders 112 and/or the tension wires 22 can be tension sensitive to avoid overexpansion of the narrow profile balloons, causing damage to a wall of the cavity in which the narrow profile balloon is positioned. The external control 110 can be further configured to monitor tension on each tension wire 22 and to stop further exertion on any tension wire 22 when that tension wire 22 reaches a threshold tension. The external control 110 can be further configured to monitor the pressure between the flexible tube of each narrow profile balloon and a wall of the aorta 104 as a respective tension wire 22 is pulled. An internal mechanical mechanism can be included that prevents further movement of the slider 112 when the threshold is met, and/or can reduce inflation of the flexible tube 20 by releasing some fluid through the valve when the threshold is met. The external control 110 can also or alternatively comprise a digital display 118 of one or both of tension on each tension wire 22 and pressure between the flexible tube and the wall of the aorta 104. The digital display 118 can be incorporated into the external control 110 or can be a separate display in communication with the external control 110.

Figure 9:
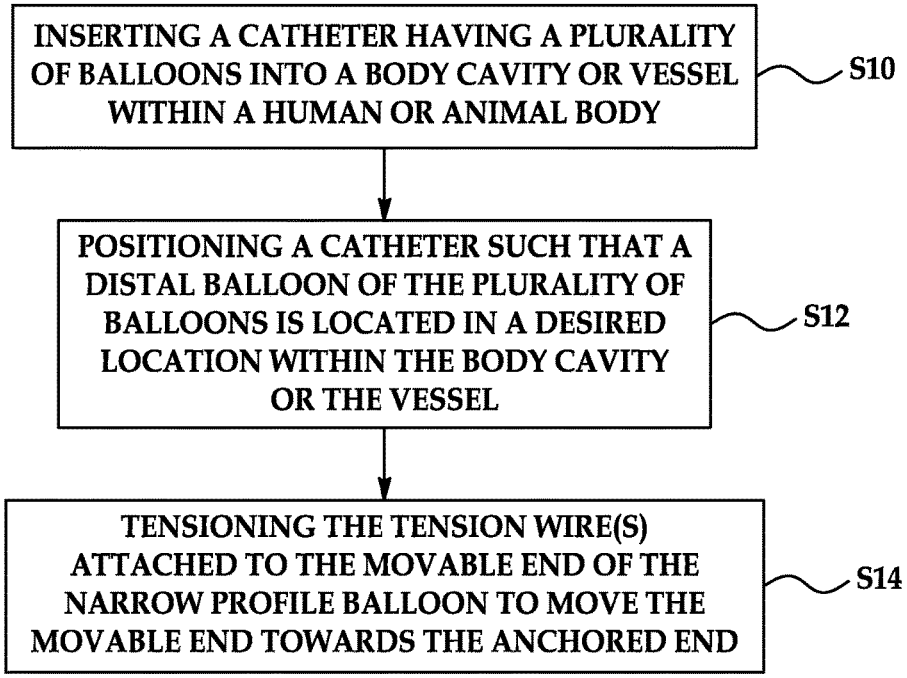
FIG. 9 is a flow diagram of a method of using the catheter with narrow profile balloons.

FIG. 9 illustrates a method of using an aortic occlusion device disclosed herein. Using an aortic occlusion device having a plurality of balloons, with at least one of the plurality of balloons being the narrow profile balloon 10 disclosed herein, one method comprises first inserting the catheter 12 into a body cavity or vessel within a human or animal body in step S10. The catheter 12 is then positioned such that a distal balloon of the plurality of balloons is located in a desired location within the body cavity or the vessel in step S12. Tension is then placed the tension wire(s) 22 attached to the movable end 16 of the narrow profile balloon 10 to move the movable end 16 towards the anchored end 14 in step S14, thereby moving the flexible tube 20 to contact a wall of the body cavity or vessel, blocking blood flow below the flexible tube 20.

The method can further include inflating the flexible tube prior to placing tension on the tension wire(s) 22 in step S14. The method can further include gradually releasing the tension on the tension wire(s) 22 attached to the movable end 16 of the narrow profile balloon 10, thereby gradually reinstating blood flow past the narrow profile balloon 10, preventing a rapid drop in afterload and blood pressure.

Also disclosed herein are selective aortic balloon occlusion devices (SABOT). The selective aortic balloon occlusion devices are used for Selective Aortic Balloon Occlusion in Trauma (SABOT) and allow for occlusion of flow through the aorta to control hemorrhage in trauma. The SABOT may also play an important role in the medical resuscitations by adjusting afterload and relative intravascular volume, as further described herein.

One embodiment of a SABOT 200 is illustrated in FIG. 10 and comprises a catheter 212 comprising an open distal end 214 and a plurality of adjustable port regions P1, P2, P3 with inflatable balloons B1, B2, B3 between adjacent adjustable port regions P1, P2, P3 and the open distal end 214 as illustrated. Each adjustable port region P1, P2, P3 is configured to move between a closed position and an open position to selectively allow fluid flow to enter the catheter 212 through the open distal end 214 and to exit the catheter 212 through one or more of the plurality of adjustable port regions P1, P2, P3 depending on an inflation pattern of the inflatable balloons B1, B2, B3. Although three inflatable balloons B1, B2, B3 and three adjustable ports P1, P2, P3 are illustrated, the number is not meant to be limiting. The adjustable ports P1, P2, P3 allow flow of blood out of the catheter 212 to selectively perfuse different regions of the body.

Although the balloons B illustrated in the figures are shown as a narrow profile balloon disclosed herein, the balloons B can be conventional balloons or a combination of conventional balloons and narrow profile balloons. As a non-limiting example, a conventional balloon may be used as the most distal balloon B1 for stability when used in the aorta, with the other balloons BN being narrow profile balloons.

The open distal end 214 can have a single opening or can have multiple apertures forming the opening as illustrated. The open distal end 214 can be configured to always be open, or can be an adjustable opening similar to the adjustable port regions PN as disclosed herein. The catheter 212 is at least partially hollow from the open distal end 214 to a location downstream of the most downstream adjustable port region to allow fluid such as blood to flow through the catheter until the location downstream of the most downstream adjustable port region.

Figure 12:
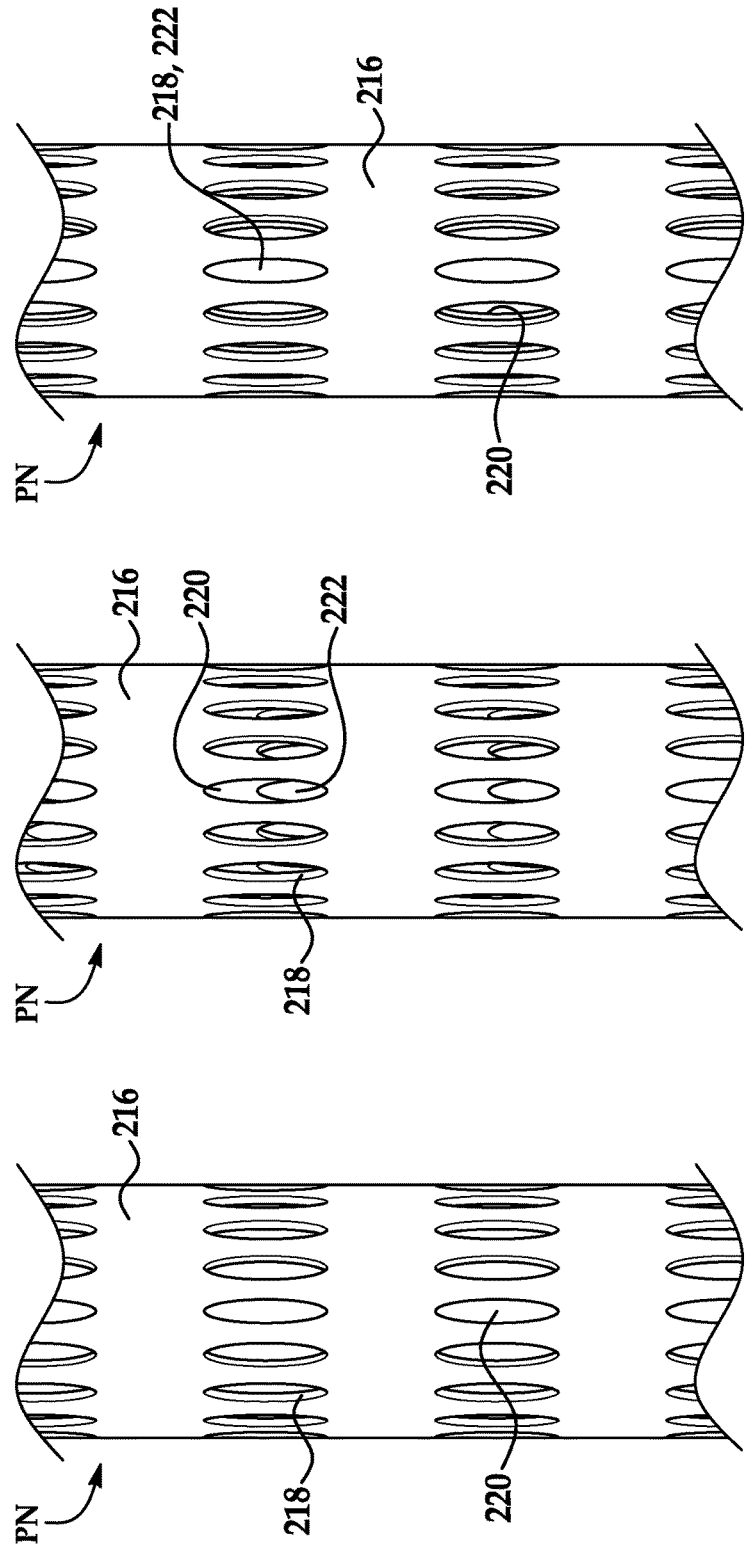
FIGS. 12A-12C are enlarged views of the adjustable port region of FIG. 11 illustrating the progression between a closed position and an open position.

Each adjustable port region has an inner perforated element, an outer perforated element, and a tension spring. The tension spring is positioned such that the ports are in a closed position by default. As illustrated in FIG. 11, each adjustable port region PN of a SABOT 200 comprises an outer catheter tube 216 having at least one outer aperture 218 there through and an inner tube 220 sized to movably fit within the outer catheter tube 216 and having at least one inner aperture 222 there through. A biasing member 224 is attached to the inner tube 220, biasing the inner tube 220 so that the inner aperture(s) 222 and the outer aperture(s) 218 are fully offset in the closed position as illustrated in FIG. 12A. The biasing member 224 is configured to move the inner tube 220 to gradually overlap the inner aperture(s) 222 and the outer aperture(s) 218 through intermediate positions shown in FIG. 12B and through to the open position, illustrated in FIG. 12C, where the inner aperture(s) 222 and the outer aperture(s) 218 are fully aligned.

The outer aperture 218 and the inner aperture 222 can be configured as a single aperture on each of the outer catheter tube 216 and the inner tube respectively or can each be a plurality of apertures 218, 222 spaced around a circumference of the outer catheter tube 216 and the inner tube 220, respectively, in one or a plurality of rows, as illustrated in the figures. Alternatively, the plurality of apertures 218, 222 can be spaced longitudinally along the outer catheter tube 216 and the inner tube 220, respectively. These configurations are provided by means of example and are not meant to be limiting.

The SABOT can further include an external controller 230 as illustrated in FIG. 13. The external controller 230 can be in separate communication with each adjustable port region PN and each inflatable balloon BN and configured to independently inflate and deflate each balloon BN and independently move each adjustable port region PN between the closed position and the open position.

As a non-limiting example, the external control 230 can have sliders 232, each slider 232 connected to biasing member 224 of an adjustable port region PN through a connection member 233 such as a wire. The sliders 232 can be individually moved to any position along a respective track 234 to thereby move the biasing member 224 to thereby move the inner tube 220 along a length of the catheter 212 to move the respective adjustable port region among closed, partially open and open positions. The sliders 232 can be configured to lock in place after being positioned to the desired point along the respective track 234, such as by pushing the slider 232 in or pulling the slider 232 outward to a locking position. The external control 230 can also be engaged with an inflation valve associated with a respective inflatable balloon BN and configured to selectively expand the inflatable balloon BN. As a non-limiting example, the external control 230 can include a valve 236 connected through a fluid supply conduit 237 between a respective inflation valve of an inflatable balloon BN and a fluid supply, such as air.

If narrow profile balloons 10 are used as disclosed herein, the external control 230 can also engage the at least one tension wire 22 of each of the narrow profile balloons 10 included in the SABOT 200 and configured to selectively pull or release each of the at least one tension wire 22 to move the flexible tube 20 of each narrow profile balloon 10 toward a wall of the body cavity or vessel. As a non-limiting example, the external control 230 can have sliders 238, each slider 238 connected to a tension wire(s) 22 of a narrow profile balloon 10. The sliders 238 can be individually moved to any position along a respective track 240 to thereby move the narrow profile balloon 10 among closed, partially open or open positions. The sliders 238 are configured to lock in place after being positioned to the desired point along the respective track 240, such as by pushing the slider 238 in or pulling the slider 238 outward to a locking position. By adjusting the tension on each biasing member 224 with a respective slider 232, the ports can be opened to varying degrees, which allows for adjustable flow at any level, independent of other levels.

The sliders 238 and/or the tension wires 22 can be tension sensitive to avoid overexpansion of the narrow profile balloons 10, causing damage to a wall of the cavity in which the narrow profile balloon 10 is positioned. The external control 230 can be further configured to monitor tension on each tension wire 22 and to stop further exertion on any tension wire 22 when that tension wire 22 reaches a threshold tension. The external control 230 can be further configured to monitor the pressure between the flexible tube of each narrow profile balloon and a wall of the body cavity or vessel as a respective tension wire 22 is pulled. An internal mechanical mechanism can be included that prevents further movement of the slider 238 when the threshold is met, and/or can reduce inflation of the flexible tube 20 by releasing some fluid through the valve 237 when the threshold is met. The external control 230 can also or alternatively comprise a digital display 118 of one or each of tension on each tension wire 22, pressure between the flexible tube 20 and the wall of the cavity or vessel, and an open or closed position of each adjustable port region PN. The digital display 118 can be incorporated into the external control 230 or can be a separate display in communication with the external control 230 by a hard wired means or a wireless means.

Another embodiment of a SABOT 250 is illustrated in FIG. 14 and comprises the catheter 212 comprising the open distal end 214 configured to be inserted into a body cavity or vessel and a first adjustable port region P1 with a first balloon B1 downstream of the open distal end 214 and upstream of the first adjustable port region P1. A second balloon B2 is positioned downstream of the first adjustable port region P1. A second adjustable port region P2 is downstream of the second balloon B2. The first adjustable port region P1 and the second adjustable port region P2 are each configured to selectively move between an open position and a closed position, wherein the open position allows flow into the open distal end 214 through the catheter 212 and exiting through one or both of the first adjustable port region P1 and the second adjustable port region P2 when in the open position, and the closed position prevents flow through one or both of the first adjustable port region P1 and the second adjustable port region P2 when in the closed position.

Figures 16, 17:
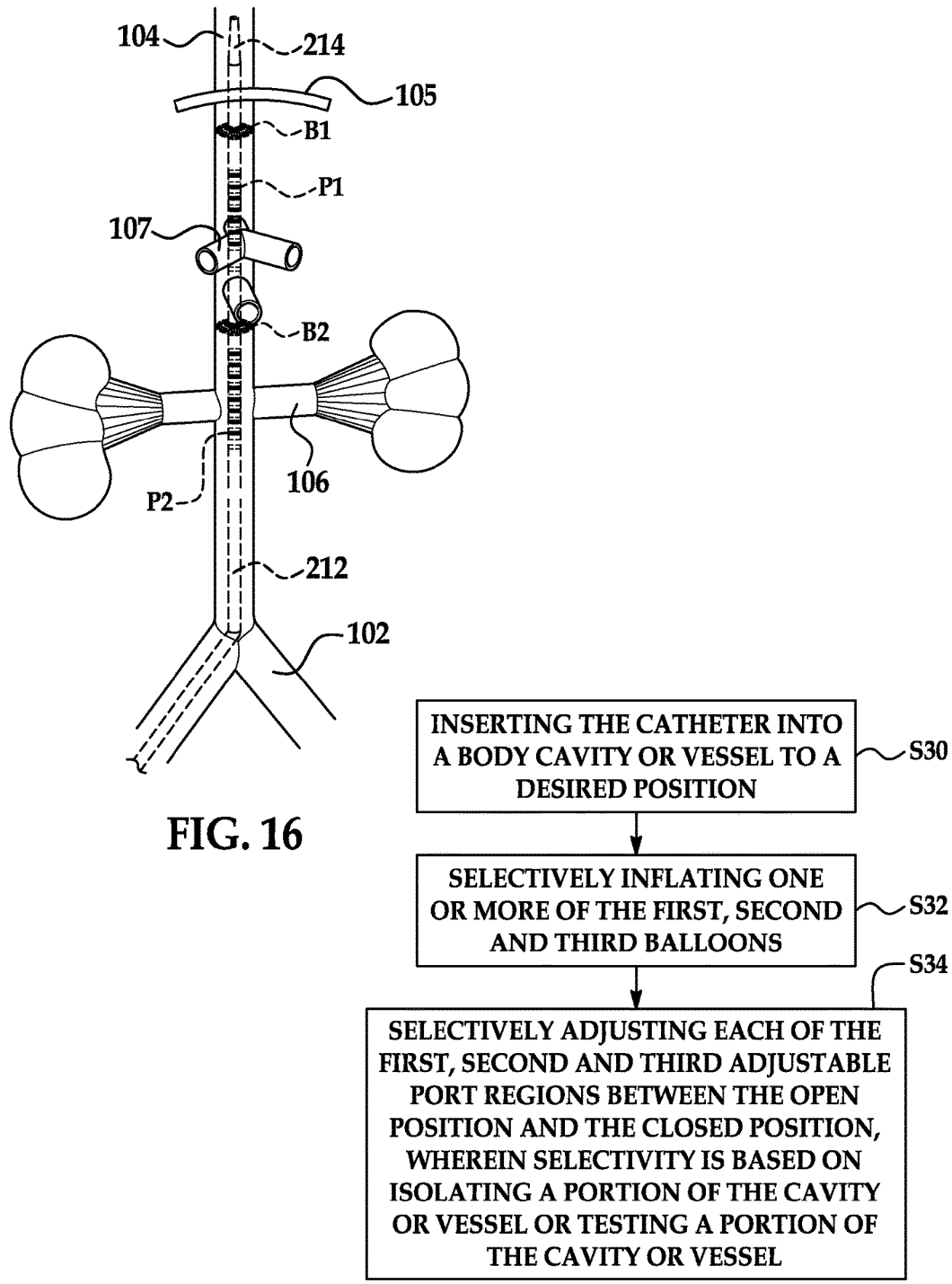
FIG. 16 is an illustration of the selective aortic balloon occlusion device of FIG. 15 in the descending aorta.
FIG. 17 is a flow diagram of a method of using the selective aortic balloon occlusion device of FIG. 10.

An example of a method of using the SABOT of FIG. 14 is illustrated in FIGS. 15 and 16. The method comprises inserting the catheter 212 into the cavity or vessel to a desired position in step S20. Once positioned, both of the first balloon B1and the second balloon B2 are selectively inflated in step S22. The first adjustable port region P1 is moved to the closed position in step S24. It is noted that the catheter 212 can be inserted with all adjustable ports in the closed positions, so moving the first adjustable port region P1 includes maintaining the first adjustable port region P1 in the closed position. The second adjustable port region P2 is moved to the open position in step S26, thereby isolating the cavity or vessel between the first balloon B1 and the second balloon B2 while allowing fluid to flow to the cavity or vessel downstream of the second balloon B2.

FIG. 16 illustrates a specific example of the SABOT of FIG. 14. In FIG. 16, the first balloon B1 and t second balloon B2 are configured to be spaced on the catheter 212 such that, when the catheter 212 is inserted in a descending aorta 104 through a femoral artery 102 of an adult human, the first balloon B1 would be positioned proximate a diaphragm 105 and the second balloon B2 would be positioned between celiac ports 107 and renal ports 106. The catheter 212 is inserted into the femoral artery 102 and into the descending aorta 104, positioning the first balloon B1 proximate the diaphragm 105, thus placing the second balloon B2 between the celiac ports 107 and the renal ports 106. Both the first balloon B1 and the second balloon B2 are selectively inflated. The first adjustable port region P1 is in the closed position and the second adjustable port region P2 is moved to the open position, thereby isolating the celiac ports 107 while allowing fluid to flow through the catheter 212 and out of the second adjustable port region P2 to the renal ports 106 and ports downstream of the renal ports 106.

Methods of using the embodiment of the SABOT 200 in FIG. 10 are also disclosed. One such method illustrated in FIG. 17 comprises inserting the catheter 212 into the cavity or vessel to a desired position in step S30, selectively inflating one or more of the first balloon B1, the second balloon B2 and the third balloon B3 in step S32 and selectively adjusting each of the first, second and third adjustable port regions P!, P2, P3 between the open position and the closed position in step S34. Selectivity is based on isolating a portion of the cavity or vessel or testing a portion of the cavity or vessel.

Figure 18:
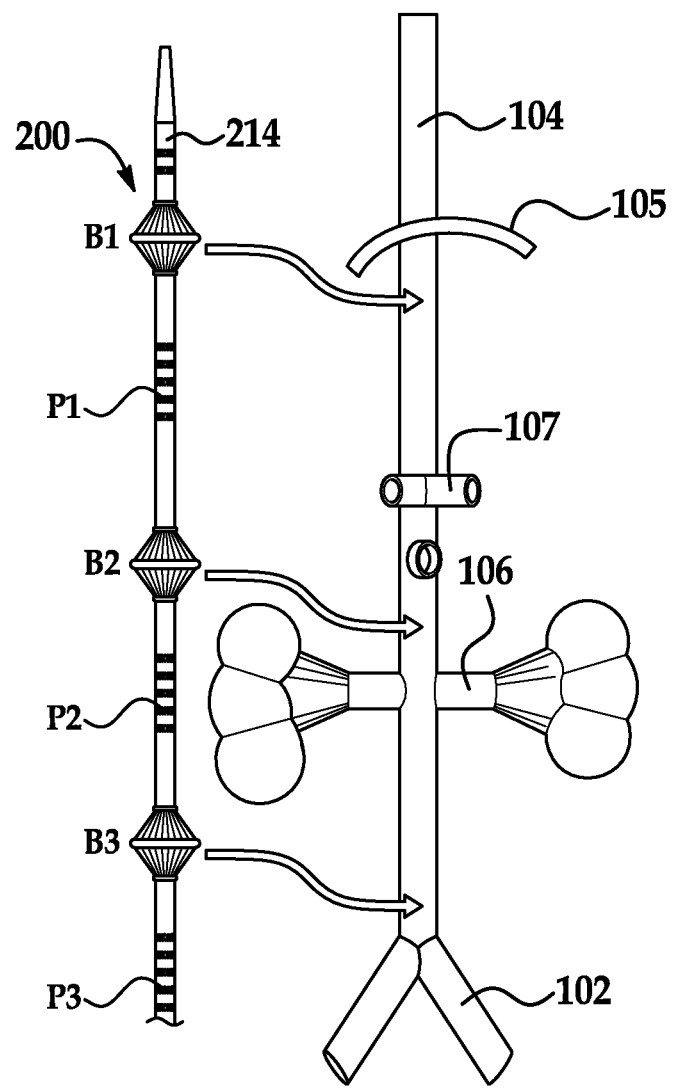
FIG. 18 is a side view of the selective aortic balloon occlusion device of FIG. 10 illustrating placement of the device along a descending aorta.

The second balloon B2 and the third balloon B3 can be configured on the catheter 212 such that when the catheter 212 is inserted in a descending aorta 104 through a femoral artery 102 of an adult human and the first balloon B1 is positioned proximate a diaphragm 105, the second balloon B2 is positioned between celiac ports 107 and renal ports 106 and the third balloon B3 is positioned between renal ports 106 and pelvic ports 102. This is illustrated in FIG. 18. Using the SABOT configured in this way, methods of use can include, but are not limited to, the following examples.

Each of the first balloon B1, the second balloon B2 and the third balloon B3 are inflated. The first adjustable port region P1 is placed in the open position while keeping ports in the second adjustable port region P2 and the third adjustable port region P3 closed, thereby allowing fluid flow through the catheter 212 to only the celiac ports 107 through the first adjustable port region P1 to test for injury to the liver and spleen.

At least the first balloon B1 and the second balloon B2 are inflated. The first adjustable port region P1 is in the closed position while opening ports in the second adjustable port region P2 and the third adjustable port region P3, thereby isolating the celiac ports 107 from fluid flow but allowing fluid flow through the catheter 212 to the renal ports 106 through the second adjustable port region P2 and pelvic ports 102 through the third adjustable port region P3.

Each of the first balloon B1, the second balloon B2 and the third balloon B3 are inflated. The first adjustable port region P1 and the second adjustable port region P2 are opened while keeping ports in the third adjustable port region P3 closed, thereby allowing fluid flow through the catheter 212 to only the renal ports 106 through the second adjustable port region P2 to test for injury to the kidneys.

At least the second balloon B2 and the third balloon B3 are inflated. The second adjustable port region P2 is closed while opening ports in the first adjustable port region P1 and the third adjustable port region P3, thereby isolating the renal ports 106 from fluid flow but allowing fluid flow through the catheter 212 to the celiac ports 107 through the first adjustable port region P1 and pelvic ports 102 through the third adjustable port region P3.

Each of the first balloon B1, the second balloon B2 and the third balloon B3 are inflated. The third adjustable port region P3 is opened while keeping ports in the first adjustable port region P1 and the second adjustable port region P2 closed, thereby allowing fluid flow through the catheter 212 to only the pelvic ports 102 through the third adjustable port region P3 to test for injury to the pelvic area.

At least the third balloon is inflated. The third adjustable port region P3 is closed while keeping ports in the first adjustable port region P1 and the second adjustable port region P2 open, thereby isolating the pelvic ports 102 from fluid flow but allowing fluid flow through the catheter 212 to the renal ports 106 through the second adjustable port region P2 and celiac ports 107 through the first adjustable port region P1.

The methods of use and treatment and testing are summarized in Table 1 below. The examples in the table are not meant to limit the methods, treatment or testing for which the SABOTs disclosed herein can be used.

TABLE 1

| Condition | Inflated Balloons | Open Ports | Closed Ports |
| --- | --- | --- | --- |
| Hypotension | B1, B2, B3 | | P1, P2, P3 |
| Test injury liver/spleen | B1, B2, B3 | P1 | P2, P3 |
| No liver injury/test Kidney | B2, B3 | P1, P2 | P3 |
| Liver injury/test kidney | B1, B2, B3 | P2 | P1, P3 |
| Isolated Kidney Injury | B2, B3 | P1, P3 | P2 |
| Liver and kidney injury/test pelvis | B1, B2, B3 | P3 | P1, P2 |
| Isolated Pelvis Injury | B3 | P1, P2 | P3 |
| BP stable | None | P1, P2, P3 | |

The distal end of the catheter can be open with inflow perforations to allow blood flow into catheter at all times. The proximal end of the catheter is closed and doesn't allow flow inside the catheter beyond the pelvic ports. The catheter is placed via the femoral artery and can be advanced under ultrasound guidance when using an echogenic (embedded with metallic material) distal tip of the catheter as a guide. Once in place, the balloons are inflated and the balloon deployment frames are expanded if the narrow profile balloons are used. Ultrasound guidance can be provided with the use of echogenic material on the frames of the narrow profile balloons. The order of balloon inflation and expansion can begin with balloon B1, then B2 followed by B3. Ports or perforations in the catheter can be opened and closed partially or completely for adjustable flow and afterload at each section independently. By inflating all balloons and closing all adjustable port catheter sections, flow is maintained to structures above the diaphragm (heart, brain, etc.). After placement confirmation and return of blood pressure, or after active serious bleeding has been excluded or corrected, ports should be opened and balloons deflated and collapsed in sequence.

With the SABOT properly placed, blood flow can be occluded with balloons and selectively opened with ports to perfuse: completely just below the diaphragm for hypovolemic shock without a known bleeding source; below the diaphragm, bypass to the liver and spleen, then adjustable flow to the renal arteries and below; and below the renals, with continuous, adjustable flow to the iliac arteries and below. With the use of balloon expansion control, sliders are tension sensitive to avoid overexpansion and vascular damage; and sliders can lock into place after adjustment. With the use of the biasing element adjustment, each area separately can be placed in closed, partial open, or complete open positions; sliders can lock into place after adjustment, and the spring loaded ports allow for gradual opening, thereby preventing a rapid drop in afterload and blood pressure. Any combination of the above can be used depending on the site of injury.

Provided below is an example of a sequence of testing that can be done with the SABOTs disclosed herein, with or without the narrow profile balloons.

Sequence: Test for Liver/Spleen Injury
  After stabilization, P1 is gradually opened, allowing flow to the liver, spleen and stomach.
    If the patient becomes unstable, the ports may be reclosed and the patient should be considered to have a liver or splenic injury.
    If blood pressure remains stable, B1 is deflated and collapsed.
Sequence: Liver/Spleen Injury Found, so Test for Renal Injury
  Next, with B1 inflated and P1 closed due to assumed liver spleen injury, P2 to the renal ports should be gradually opened.
    If blood pressure becomes unstable, reclose ports and consider a renal injury.
    If patient remains stable after opening the renal ports P2, keep them open to selectively perfuse kidneys.
Sequence: No Liver/Spleen or Renal Injury
  After exclusion of Liver/Spleen and Renal injury, B1 and B2 should be deflated; P1 (celiac) and P2 (renal) remain open.
Sequence: Pelvic/Lower Extremity Injury
  With successful reperfusion of liver/spleen and renals, the pelvic ports (P3) should be gradually opened.
    If blood pressure is unstable after gradually attempting pelvic/lower extremity reperfusion, the ports should be reclosed and a pelvic/lower extremity bleeding source should be assumed.
    Do not deflate B3 in this circumstance.

Isolated Renal Injury
  If BP stable with Liver/Spleen reperfusion, but unstable with renal reperfusion, and stable with pelvic reperfusion, keep B2 and B3 expanded and inflated and P1 (celiac) and P3 (pelvic) open.

Provided below are examples of other uses of the SABOTs disclosed herein, with or without the narrow profile balloons.

1. Traumatic Shock:
  a. Multi-level balloons, blood flow, Ports between the levels of the balloons to selectively and independently open areas of perfusion
  b. Allows to isolate hemorrhaging areas, perfuse areas distant to hemorrhage so as to decrease amount of lactic acid build-up and permanent ischemic injury.
2. Post-Arrest Cardiogenic Shock:
  c. Stunned myocardium after cardiopulmonary arrest and return of spontaneous circulation (ROSC) would not have to work as hard if internal cross-clamping of aorta occurred with this device. This device would allow gradual level reperfusion of the organs, gradually increasing the amount of work the myocardium does as it is recovering.
3. Septic Hypotensive Shock
  d. In septic shock, the body preferentially perfuses the vital organs (brain, heart, kidneys) by shunting away from less essential (mesenteric structures, periphery). In the case of massive vasodilatation due to endovascular toxin release, this device would assist in closing off or partially perfusing certain areas—an assistive shunt of sorts.
4. Anaphylactic Hypotensive Shock
  e. Massive vasodilation occurs. Blood pressure drop could be aided by shunting blood to vital organs (brain, heart, kidneys) and effectively shunting blood away from less vital organs for a brief period of time. Then you can use the device to gradual open and reperfuse other arterial beds as body is responding to medication.

Other potential markets for the SABOTs disclosed herein include, but are not limited to neurogenic shock, resuscitation with unclear etiology (post-arrest), emergent bypass of leaking AAA, and pre-operative placement for immediate control of intraoperative bleeding.

Table 2 below is a brief comparison of the SABOTs disclosed herein with the conventional devices.

TABLE 2

| Conventional Devices | SABOT |
| --- | --- |
| All or nothing approach | Segmental perfusion possible |
| Poor control over reperfusion | Sequential and partial reperfusion |
| Can't perfuse kidneys, bowel or lower extremities if other intrabdominal bleeding exists | Able to perfuse specific vascular beds in isolation (kidneys, liver/spleen, lower extremities) |
| Large balloons | Narrow-profile balloon allows for precise placement |
| Crude estimate of pressure applied to aortic walls | Controlled pressure to prevent vascular damage |

The SABOT allows bypass of injured organs selectively via the ported catheter. With conventional devices, no bypass perfusion is possible. If injury is at the level of the liver or spleen (celiac level), the supra celiac balloon must remain inflated preventing perfusion to the entire body below the diaphragm.

The SABOT has port size adjustment, which provides for a more precise and gradual reperfusion thereby eliminating a sudden drop in afterload and thus blood pressure with recurrent shock. This also decreases the rate of inflammatory mediator release allowing for the gradual adjustment of the circulatory system and involved organs to the onslaught of shock-inducing agents. With the conventional devices, reperfusion is accomplished via deflation of balloons above the site of injury which is inherently inconsistent and offers poor control.

The narrow profile balloons disclosed herein have an expansion frame upon which the balloon is mounted that can be attached to a slide and the tension applied for expansion as well as the pressure within the balloon can be quantitated in order to prevent vascular injury. Conventional devices have no expansion frame.

The narrow profile balloon allows more precise placement and therefore can be positioned in the highly important narrow space (for example, approximately 2 cm.) between the celiac and renal arteries, thus allowing bypass to the kidney's while preventing flow to the liver, spleen, intestine, pelvis and lower extremities. Conventional (wide) profile balloons make precise positioning impossible. The metal supports in the expansion frame can be used for ultrasonographic placement and verification. Metal impregnation (or other sound reflective material) in the catheter tip allows easier ultrasonographic identification of the catheter tip.

The SABOT is designed to be used with a reusable external controller for precise balloon and port control. No such device exists for use with a conventional device.

The SABOT is designed to be placed in the femoral artery via currently accepted protocols which involves less risk, larger access and less cumbersome than a carotid artery approach. Conventional devices are designed to be placed via the carotid artery.

The above-described aspects, examples, and implementations have been described in order to allow easy understanding of the disclosure are not limiting. On the contrary, the disclosure covers various modifications and equivalent arrangements included within the scope of the appended claims, which scope is to be accorded the broadest interpretation so as to encompass all such modifications and equivalent structure as is permitted under the law.

What is claimed is:
1. A selective aortic balloon occlusion device comprising:
  a catheter comprising:
    a distal end configured to be inserted into a body cavity or vessel, the distal end having at least one opening;
    a first balloon downstream of the distal end;
    a first adjustable port region downstream of the first balloon;
    a second balloon downstream of the first adjustable port region; and
    a second adjustable port region downstream of the second balloon, the first adjustable port region and the second adjustable port region each configured to selectively individually move between an open position and a closed position, wherein:
      the open position allows flow into the distal end through the catheter and exiting through an opened adjustable port region; and
      the closed position prevents flow through a closed adjustable port region,
    wherein each of the first adjustable port region and the second adjustable port region comprises:
      an outer catheter tube having at least one outer aperture there through;

an inner tube sized to movably fit within the outer catheter tube and having at least one inner aperture there through; and a biasing member attached to the inner tube, biasing the inner tube so that the at least one inner aperture and the at least one outer aperture are offset in the closed position, the biasing member configured to move the inner tube to gradually overlap the at least one inner aperture and the at least one outer aperture through intermediate positions to the open position, where the at least one inner aperture and the at least one outer aperture are fully aligned.

2. The selective aortic balloon occlusions device of claim 1, wherein the biasing member is a spring.

3. The selective aortic balloon occlusion device of claim 1, wherein the at least one outer aperture and the at least one inner aperture are each a plurality of apertures spaced around a circumference of the outer catheter tube and the inner tube respectively.

4. The selective aortic balloon occlusion device of claim 3, wherein the plurality of apertures spaced around the circumference of the outer catheter tube and the inner tube respectively are each configured to be in a plurality of rows.

5. The selective aortic balloon occlusion device of claim 1, wherein each of the at least one outer aperture and the at least one inner aperture are a plurality of apertures spaced longitudinally along the outer catheter tube and the inner tube, respectively.

6. The selective aortic balloon occlusion device of claim 1 further comprising:
an external controller in separate communication with the first adjustable port region, the second adjustable port region, the first balloon and the second balloon and configured to:
independently inflate and deflate each of the first balloon and the second balloon; and
independently move the first adjustable port region between the closed position and the open position and the second adjustable port region between the closed position and the open position.

7. The selective aortic balloon occlusion device of claim 1, wherein the first balloon and the second balloon are configured to be spaced on the catheter such that, when the catheter is inserted in a descending aorta through a femoral artery of an adult human, the first balloon is positioned proximate a diaphragm and the second balloon is positioned between celiac ports and renal ports.

8. A method of using the selective aortic balloon occlusion device of claim 7 comprising:
inserting the catheter into the femoral artery and into the descending aorta, positioning the first balloon proximate the diaphragm, thus placing the second balloon between the celiac ports and the renal ports;
selectively inflating both the first balloon and the second balloon;
maintaining or moving the first adjustable port region to the closed position; and
moving the second adjustable port region to the open position, thereby isolating the celiac ports while allowing fluid to flow through the catheter and out of the second adjustable port region to the renal ports and ports downstream of the renal ports.

9. A method of using the selective aortic balloon occlusion device of claim 1 comprising:
inserting the catheter into the cavity or vessel to a desired position;
selectively inflating both the first balloon and the second balloon;
maintaining or moving the first adjustable port region to the closed position; and
moving the second adjustable port region to the open position, thereby isolating the cavity or vessel between the first balloon and the second balloon while allowing fluid to flow to the cavity or vessel downstream of the second balloon.

10. The selective aortic balloon occlusion device of claim 1 further comprising: a third balloon downstream of the second adjustable port region; and a third adjustable port region downstream of the third balloon, wherein the third adjustable port region is configured to move between an open position and a closed position.

11. The selective aortic balloon occlusion device of claim 10, further comprising:
an external controller in independent communication with each of the first adjustable port region, the second adjustable port region, the third adjustable port, the first balloon, the second balloon and the third balloon and configured to:
independently inflate and deflate each of the first balloon, the second balloon and the third balloon; and
independently move each of the first adjustable port region, the second adjustable port region, and the third adjustable port region between a respective closed position and open position.

12. The selective aortic balloon occlusion device of claim 10, wherein the second balloon and the third balloon are configured on the catheter such that when the catheter is inserted in a descending aorta through a femoral artery of an adult human and the first balloon is positioned proximate a diaphragm, the second balloon is positioned between celiac ports and renal ports and the third balloon is positioned between renal ports and pelvic ports.

13. A method of using the selective aortic balloon occlusion device of claim 10 comprising:
inserting the catheter into the cavity or vessel to a desired position;
selectively inflating one or more of the first balloon, the second balloon and the third balloon; and
selectively adjusting one or more of the first, second and third adjustable port regions between the open position and the closed position.

14. The method of claim 13, wherein the second balloon and the third balloon are configured on the catheter such that when the catheter is inserted in a descending aorta through a femoral artery of an adult human and the first balloon is positioned proximate a diaphragm, the second balloon is positioned between celiac ports and renal ports and the third balloon is positioned between renal ports and pelvic ports, the method comprising:
inflating each of the first balloon, the second balloon and the third balloon; and
opening ports in the first adjustable port region while keeping ports in the second adjustable port region and the third adjustable port region closed, thereby allowing fluid flow through the catheter to only the celiac ports through the first adjustable port region to test for injury to the liver and spleen.

15. The method of claim 13, wherein the second balloon and the third balloon are configured on the catheter such that when the catheter is inserted in a descending aorta through a femoral artery of an adult human and the first balloon is positioned proximate a diaphragm, the second balloon is positioned between celiac ports and renal ports and the third balloon is positioned between renal ports and pelvic ports, the method comprising:

inflating at least the first balloon and the second balloon; and closing ports in the first adjustable port region while keeping ports in the second adjustable port region and the third adjustable port region open, thereby isolating the celiac ports from fluid flow but allowing fluid flow through the catheter to the renal ports through the second adjustable port region and pelvic ports through the third adjustable port region.

16. The method of claim 13, wherein the second balloon and the third balloon are configured on the catheter such that when the catheter is inserted in a descending aorta through a femoral artery of an adult human and the first balloon is positioned proximate a diaphragm, the second balloon is positioned between celiac ports and renal ports and the third balloon is positioned between renal ports and pelvic ports, the method comprising:

inflating each of the first balloon, the second balloon and the third balloon; and opening ports in the first adjustable port region and the second adjustable port region while keeping ports in the third adjustable port region closed, thereby allowing fluid flow through the catheter to only the renal ports through the second adjustable port region to test for injury to the kidneys.

17. The method of claim 13, wherein the second balloon and the third balloon are configured on the catheter such that when the catheter is inserted in a descending aorta through a femoral artery of an adult human and the first balloon is positioned proximate a diaphragm, the second balloon is positioned between celiac ports and renal ports and the third balloon is positioned between renal ports and pelvic ports, the method comprising:

inflating at least the second balloon and the third balloon; and closing ports in the second adjustable port region while keeping ports in the first adjustable port region and the third adjustable port region open, thereby isolating the renal ports from fluid flow but allowing fluid flow through the catheter to the celiac ports through the first adjustable port region and pelvic ports through the third adjustable port region.

18. The method of claim 13, wherein the second balloon and the third balloon are configured on the catheter such that when the catheter is inserted in a descending aorta through a femoral artery of an adult human and the first balloon is positioned proximate a diaphragm, the second balloon is positioned between celiac ports and renal ports and the third balloon is positioned between renal ports and pelvic ports, the method comprising:

inflating each of the first balloon, the second balloon and the third balloon; and opening ports in the third adjustable port region while keeping ports in the first adjustable port region and the second adjustable port region closed, thereby allowing fluid flow through the catheter to only the pelvic ports through the third adjustable port region to test for injury to the pelvic area.

19. The method of claim 13, wherein the second balloon and the third balloon are configured on the catheter such that when the catheter is inserted in a descending aorta through a femoral artery of an adult human and the first balloon is positioned proximate a diaphragm, the second balloon is positioned between celiac ports and renal ports and the third balloon is positioned between renal ports and pelvic ports, the method comprising:

inflating at least the third balloon; and closing ports in the third adjustable port region while keeping ports in the first adjustable port region and the second adjustable port region open, thereby isolating the pelvic ports from fluid flow but allowing fluid flow through the catheter to the renal ports through the second adjustable port region and celiac ports through the first adjustable port region.

\* \* \* \* \*